United States Patent
Labyed

(10) Patent No.: US 12,089,995 B2
(45) Date of Patent: *Sep. 17, 2024

(54) ULTRASOUND MEDICAL IMAGING WITH OPTIMIZED SPEED OF SOUND BASED ON FAT FRACTION

(71) Applicant: Siemens Medical Solutions USA, Inc., Malvern, PA (US)

(72) Inventor: Yassin Labyed, Carlsbad, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,448

(22) Filed: Aug. 29, 2023

(65) Prior Publication Data
US 2023/0404537 A1 Dec. 21, 2023

Related U.S. Application Data

(63) Continuation of application No. 16/456,121, filed on Jun. 28, 2019, now Pat. No. 11,779,312.

(51) Int. Cl.
| | | |
|---|---|---|
| *A61B 8/08* | (2006.01) | |
| *A61B 8/00* | (2006.01) | |
| *A61B 8/14* | (2006.01) | |
| *G01S 7/52* | (2006.01) | |
| *G01S 15/89* | (2006.01) | |

(52) U.S. Cl.
CPC ............. *A61B 8/5207* (2013.01); *A61B 8/14* (2013.01); *A61B 8/4483* (2013.01); *A61B 8/461* (2013.01); *A61B 8/488* (2013.01); *A61B 8/481* (2013.01); *G01S 7/52049* (2013.01); *G01S 15/8927* (2013.01)

(58) Field of Classification Search
CPC ... G01S 7/52049; G01S 7/539; G01S 7/52036
See application file for complete search history.

(56) References Cited

U.S. PATENT DOCUMENTS

| | | |
|---|---|---|
| 2011/0082372 A1 | 4/2011 | Tateyama |
| 2013/0178740 A1 | 7/2013 | Han |
| 2017/0032519 A1 | 2/2017 | Thornton et al. |

(Continued)

FOREIGN PATENT DOCUMENTS

| | | |
|---|---|---|
| CN | 105930665 A | 9/2016 |
| JP | 4711583 B2 | 6/2011 |

OTHER PUBLICATIONS

Imbault, Marion, et al. "Ultrasonic fat fraction quantification using in vivo adaptive sound speed estimation." Physics in Medicine & Biology 63.21 (2018): pp. 1-16.

(Continued)

*Primary Examiner* — Joel Lamprecht
*Assistant Examiner* — Nyrobi Celestine

(57) ABSTRACT

For ultrasound imaging with an ultrasound scanner, fat fraction of the tissue is measured. The fat fraction may be measured without access to channel data, such as from beamformed data. The speed of sound varies with the fat fraction of tissue, so the fat fraction is used to set the speed of sound in beamforming. Imaging the tissue using the fat fraction-based optimization for speed of sound may provide better images than imaging with an assumed speed.

20 Claims, 1 Drawing Sheet

(56) References Cited

U.S. PATENT DOCUMENTS

| | | |
|---|---|---|
| 2017/0224308 A1 | 8/2017 | Labyed |
| 2018/0125451 A1 | 5/2018 | Duncan |
| 2018/0161015 A1 | 6/2018 | Hollaender et al. |
| 2018/0289323 A1 | 10/2018 | Labyed |
| 2019/0029649 A1 | 1/2019 | Tanigawa et al. |
| 2019/0038220 A1 | 2/2019 | Rubin et al. |
| 2019/0336108 A1* | 11/2019 | Hope Simpson ... G01S 15/8915 |
| 2020/0196987 A1* | 6/2020 | Kim .................. G01S 7/52049 |

OTHER PUBLICATIONS

Imbault, Marion, et al. "Robust sound speed estimation for ultrasound-based hepatic steatosis assessment." Physics in Medicine & Biology 62.9 (2017): pp. 3582-3598.

* cited by examiner

ULTRASOUND MEDICAL IMAGING WITH OPTIMIZED SPEED OF SOUND BASED ON FAT FRACTION

RELATED APPLICATION

This application is a continuation of U.S. application Ser. No. 16/456,121, filed Jun. 28, 2019, which is hereby incorporated by reference in its entirety.

BACKGROUND

The present embodiments relate to ultrasound imaging of soft tissue. In ultrasound imaging of soft tissue, such as liver imaging, the speed of sound in the tissue is assumed to be 1540 m/s. The assumed speed of sound is used for focusing or beamforming in ultrasound scanning with an array. The actual speed of sound is different for different tissues and/or patients. As a result, the assumed 1540 m/s may lead to suboptimal images.

The speed of sound is difficult to measure with ultrasound. Often, the assumed speed is used. Alternatively, the speed of sound used in beamforming is found through variation to a few discrete values. The value that yields the optimal image quality measured based on a combination of image brightness, contrast, lateral resolution, and lateral bandwidth may be selected. These measurements require access to channel data, which may not be available.

SUMMARY

By way of introduction, the preferred embodiments described below include methods, instructions, and systems for ultrasound imaging with an ultrasound scanner. Fat fraction of the tissue is measured. The fat fraction may be measured without access to channel data, such as from beamformed data. The speed of sound varies with the fat fraction of tissue, so the fat fraction is used to set the speed of sound in beamforming. Imaging the tissue using the fat fraction-based optimization may provide better images than imaging with an assumed speed.

In a first aspect, a method is provided for ultrasound imaging with an ultrasound scanner. Fat fraction for a liver of a patient is estimated. A speed of sound for the liver is determined from the fat fraction. A beamformer of the ultrasound scanner is configured based on the determined speed of sound. The liver of the patient is imaged with the beamformer as configured based on the determined speed of sound.

In a second aspect, a system is provided for ultrasound medical imaging. A beamformer is configured to scan tissue in a patient, with a transducer, based on a first speed of sound and a second speed of sound. An image processor is configured to estimate a value for fat fraction of tissue of the patient from beamformed samples output by the beamformer using the first speed of sound, to set the second speed of sound from the fat fraction, and to generate an image of the tissue from beamformed samples output by the beamformer using the second speed of sound as set from the fat fraction. A display is configured to display the image of the tissue.

In a third aspect, a method is provided for optimized speed of sound in ultrasound medical scanner. A fat fraction of tissue in a patient is measured. A beamformer focus profile is set based on the fat fraction. The tissue of the patient is scanned by the ultrasound medical scanner using the beamformer focus profile. An image of the tissue is generated from results of the scanning.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound liver or other soft tissue imaging uses optimized speed of sound based on measured fat fraction. The fat fraction may be ultrasonically-derived. The beamforming speed of sound adapts to the bioacoustic variations of each patient based on the measured fat fraction for that patient. Studies have shown that speed of sound in the liver is proportional to the fat fraction. The beamforming sound speed is based on automatic measurements of the ultrasonically-derived or other measures of fat fraction for the tissue being imaged.

Figure 1:
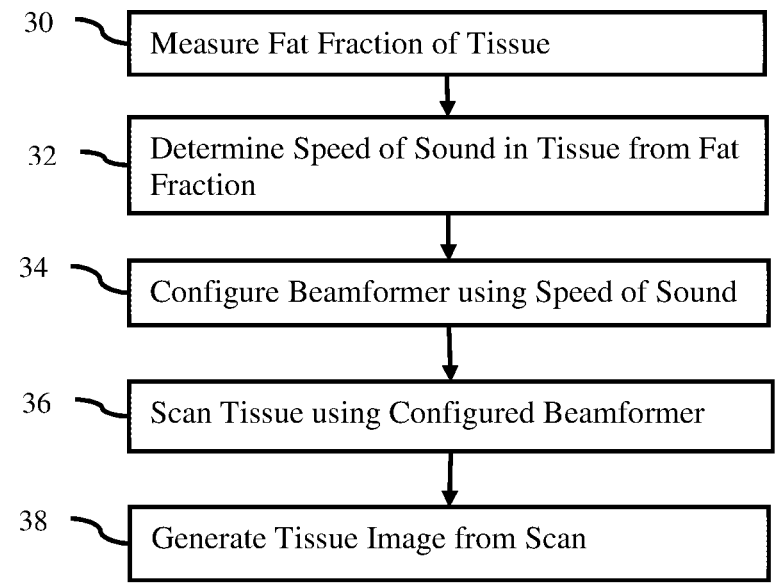
FIG. 1 is a flow chart diagram of one embodiment of a method for ultrasound imaging with an ultrasound scanner using speed of sound optimized from fat fraction.

FIG. 1 shows one embodiment of a method for ultrasound imaging with an ultrasound medical scanner. The speed of sound is optimized based on the fat fraction. The ultrasound medical scanner uses the fat-fraction-based speed of sound to image the tissue, providing improved images as compared to using a default speed of sound. Better or more accurate diagnosis by physicians or sonographers may result from the improved images of the patient tissue.

Figure 2:
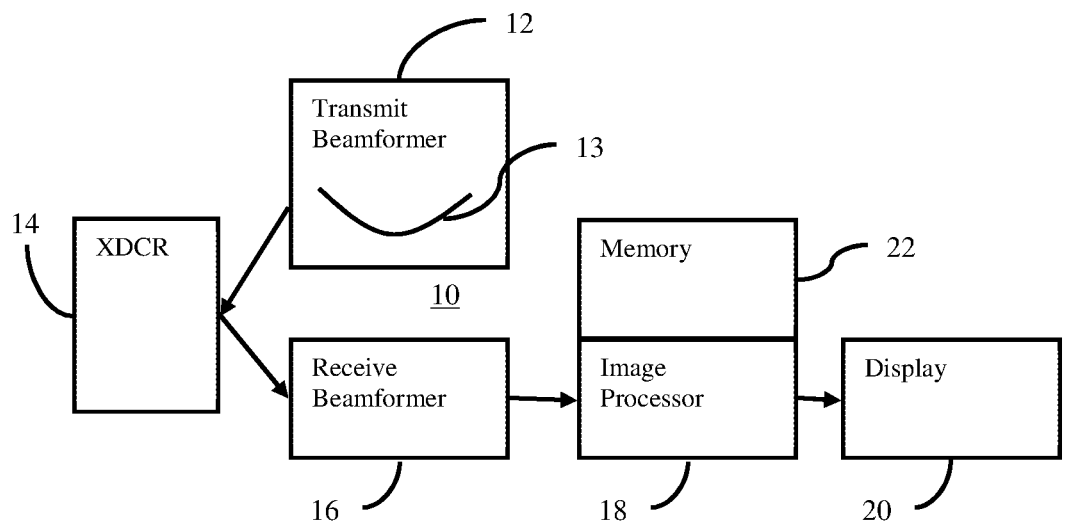
FIG. 2 is a block diagram of one embodiment of a system for ultrasound medical imaging using speed of sound from fat fraction.

The method is implemented by the system of FIG. 2 or a different system. A medical diagnostic ultrasound scanner performs the measurements by acoustically generating the waves and measuring the responses with a beamformer. An image processor of the scanner, computer, server, or other device estimates the fat fraction, determines the speed of sound, configures the beamformer based on the determined speed of sound, causes scanning of the tissue with the configured beamformer, and generates an image. A display device, network, or memory is used to output the estimated image.

Additional, different, or fewer acts may be provided. For example, act 38 may not occur. The acts are performed in the order described or shown (e.g., top to bottom or numerically), but may be performed in other orders.

In act 30, a processor, such as an image processor, estimates or measures the fat fraction of tissue of a patient. The estimation or measure is by scanning the patient. Alternatively, the estimation or measure is by look-up, such as from a computerized medical record of the patient. The estimate or measure is obtained from a database, memory, computer network transfer, or scan of the patient.

The fat fraction is specific to the patient. One or more characteristics of the patient are used to obtain the fat fraction for that patient. Some patients may have the same or similar fat fraction, but different patients may have different fat fractions.

In one embodiment, the tissue is the liver of the patient. The fat fraction for the liver of the patient is obtained. The liver example is used herein. In other embodiments, the tissue is from the kidney, bladder, breast, heart, muscle, or other soft tissue of the patient.

The fat fraction may be obtained from a magnetic resonance scan of the patient, such as measured with a magnetic resonance proton density fat fraction (MR-PDFF) scan. Other modalities may be used to measure or estimate the fat fraction. In another embodiment, the fat fraction is obtained from an ultrasound scan. Since the fat fraction is used to determine the speed of sound in the tissue (e.g., liver tissue) for ultrasound imaging, the ultrasound scanner estimating or measuring the fat fraction may be more cost and time effective and more convenient.

For ultrasound estimation of the fat fraction of the tissue, the ultrasound medical scanner determines the scatter and attenuation from scanning the tissue in one embodiment. Other combinations of quantitative ultrasound parameters may be used. The complexity of human tissue may be measured using multiple quantitative ultrasound parameters for accurate characterization of that tissue. For example, liver fat fraction is estimated using a multi-parametric approach that combines quantitative parameters extracted from the received signals of different wave phenomena, such as scattering and attenuation of longitudinal waves, propagation and attenuation of shear waves, and/or propagation and attenuation of on-axis waves from acoustic radiation force impulse (ARFI) excitation. U.S. Published Patent Application No. 2018/0289323 discloses estimation of fat fraction using ultrasound.

In one embodiment, liver fat fraction is estimated by transmitting and receiving a sequence of pulses to estimate scattering parameters and by transmitting and receiving a sequence of pulses to obtain shear wave parameters. The estimation may include transmitting and receiving a sequence of pulses to estimate parameters from axial displacements caused by acoustic radiation force impulses (ARFI). The parameters are estimated and combined to estimate the fat fraction. Other information may be included in the estimation of the fat fraction, such as non-ultrasound data (e.g., blood biomarker). A look-up table based on empirical study may be used to relate values of the various parameters to values of fat fraction.

An ultrasound scanner generates a measure of scattering in tissue from a scan of a patient. To measure the scatter, the ultrasound scanner scans the tissue with ultrasound. A sequence of transmit and receive events is performed to acquire the signals to estimate the quantitative ultrasound scatter parameters. These parameters measure the tissue's response to a longitudinal wave transmitted from an ultrasound scanner. The scattering or echo of the longitudinal wave impinging on the tissue is measured.

Any measure of scatter may be used, such as a spectral slope of a logarithm of frequency-dependent backscatter coefficient. For example, attenuation coefficient is measured. A reference-phantom method is used, but other measures of the attenuation coefficient may be used. Acoustic energy has an exponential decay as a function of depth. A measure of acoustic intensity as a function of depth before or without depth gain correction is performed. To remove system effects, the measurement is calibrated based on measures of acoustic intensity as a function of depth in a phantom. The measurement may be subject to less noise by averaging over a one, two, or three-dimensional region. The beamformed samples or acoustic intensity may be converted to the frequency domain, and the calculation performed in the frequency domain.

The attenuation is measured as a slope of intensity as a function of depth. Other measures of attenuation may be used, such as attenuation of a shear wave over distance or time. Tissue displacement as a function of depth from an ARFI induced longitudinal wave may be used to find attenuation of the tissue. The amount of maximum displacement, displacement as a function of depth, and/or displacement as a function of time is used to calculate the attenuation. Other propagation measures may be used instead of or as the attenuation. For example, a measure of shear wave propagation or a measure of on-axis displacement (e.g., ARFI measure) may be used.

The fat fraction may be determined from the attenuation and scatter or from other combinations of quantitative ultrasound information. Values for the attenuation or propagation and backscatter measurements are input to a machine-learned classifier or look-up table, which outputs values of the fat fraction. The machine-trained classifier provides a nonlinear model. The look-up table may provide a linear model. A predetermined or programmed function relates the input values to the output values. The function and/or weights used in the function may be determined experimentally. For example, the weights are obtained by a least square minimization using magnetic resonance-proton density fat fraction (MR-PDFF) values.

Other approaches to measuring fat fraction by the ultrasound medical scanner may be used. For measuring with ultrasound, a beamformer of the scanner is configured for scanning. The focus of transmit beams and receive beams, including dynamic focusing on receive, is based on a delay or phase profile. The distance and speed of sound are used to determine an amount of phasing or delay applied to signals to or from each element of an array of elements for focusing.

The speed of sound, for measuring the fat fraction, is a current speed of sound. For example, a default speed of sound value (e.g., 1540 m/s) is used. The beamformer focus profile given the focal location and the speed of sound is selected and used by the beamformer in transmit and/or receive focusing. Different profiles are used for different focal locations and/or different speeds of sound. In another example, the speed of sound as previously set based on a previous measure of fat fraction is used. The scanning to measure the fat fraction is based on the current value for speed of sound.

Imaging may occur while measuring or estimating the fat fraction. For example, B-mode imaging is performed to place and maintain a field of view of the transducer at the desired tissue. Once the field of view is at the desired location within the patient, the scanning for estimating the fat fraction is performed. The imaging continues while fat fraction is estimated. Alternatively, the imaging ceases while the fat fraction is estimated.

In act 32, a processor, such as an image processor, determines a speed of sound for the tissue (e.g., liver) from the fat fraction. The fat fraction, with or without another variable or variables, is used to determine the speed of sound.

A calculation may be used. A function relating the fat fraction to the speed of sound is used. By knowing the value of the fat fraction, the speed of sound is calculated. For example, Wood's equation may be used which is a function relating the speed of sound to density and fat fraction:

$$c = \frac{1}{\sqrt{\left(\frac{\varphi_f}{k_f} + \frac{(1-\varphi_f)}{k_b}\right)(\varphi_f \rho_f + (1-\varphi_f)\rho_b)}}$$

where c is speed of sound, $\varphi_f$ is fat fraction, $\rho_f$ is fat density, $\rho_b$ is background material density, $k_f$ is fat bulk modulus, and $k_b$ is background material bulk modulus. The density and bulk moduli are assumed. Alternatively, the density is measured, such as from average attenuation or backscatter, or derived from bulk modulus. Other functions may be used.

Instead of a calculation, a look-up table or other model relating fat fraction to speed of sound may be used. Other models may include a machine-learned classifier that was trained to output speed of sound based on input of fat fraction with or without other inputs. As a look-up table, the fat fraction may be input to directly output or look-up the speed of sound. In one example, ranges of fat fraction (e.g., % of tissue being fat) measured from ultrasound (i.e., ultrasound-determined fat fraction (UDFF)) map directly to speeds of sound (SOS). This example table may be:

UDFF (%)=[0-5, 5-10, 10-15, 15-20, 20-25, 25-30, 35-40]

SOS (m/s)=[1540, 1520, 1510, 1500, 1490, 1480, 1470, 1460], where UDFF of 0-5% maps to SOS of 1540 m/s, UDFF 5-10% maps to SOS of 1520 m/s, and so on. Other tables relating different values and/or ranges to each other may be used.

A value for speed of sound is determined. Alternatively, beamformer focus profiles are determined as the speed of sound. One or more profiles using the appropriate speed of sound are selected.

In act 34, the processor, such as the image processor and/or a beamformer controller, configures a beamformer of the ultrasound scanner based on the determined speed of sound. The beamformer uses the speed of sound for focusing transmit and/or receive beams during ultrasound scanning. Any type of ultrasound scanning may be provided, such as B-mode or Doppler (e.g., color or flow mode).

The beamformer uses delay and/or phase profiles for each focal location used in transmit and/or receive. The profiles are the same or different for different locations. The profiles are based, in part, on the distance from respective elements to the focal location within the patient. The profiles are also based on the speed of sound to provide the travel time of acoustic energy from the elements to the focal location and/or from the focal location to the elements (i.e., the speed of acoustic energy along the distance). The speed of sound is used to configure the beamformer with the desired delay and/or phase profile or profiles for scanning to image.

A beamformer focus profile (e.g., delay or phase profile) is set based on the fat fraction. The beamformer of the ultrasound medical scanner is configured to operate with a given speed of sound based on the fat fraction. The speed of sound itself is set and the profiles calculated therefrom, or the fat fraction maps to one or more focus profiles, which incorporate the speed of sound. In either approach, the speed of sound is determined from the fat fraction. The beamformer focus profile is based on the speed of sound.

Rather than continuing to use a current or default speed of sound, the speed of sound based on the measured or estimated fat fraction is used. The value of the speed of sound or profile incorporating the speed of sound is changed (e.g., altered or replaced) based on the fat fraction. The changed value or profile is for the speed of sound based on the fat fraction for the patient being imaged for subsequent imaging.

In act 36, the ultrasound medical scanner scans the tissue of the patient. The beamformer, as configured by the focus profile or profiles, transmits acoustic beams and/or forms receive beams from acoustic echoes. An array of elements of the transducer transduce between acoustic and electrical energies. The beamformer includes channels connected to the elements. The beamformer generates relatively delayed or phased electrical waveforms for the elements of a transmit aperture using the focus profile. The transducer converts the electrical waveforms into acoustic energy, which causes constructive interference at the focal location and along a scan line as a transmit beam. Acoustic echoes received at the elements are converted to electrical signals for the channels. The beamformer relatively delays and/or phases the electrical signals from the different elements in the receive aperture and combines the delayed or phased signals. Dynamic focusing where the focus shifts over time along a receive line by using different focus profiles due to the different locations may be used. The combination by beamforming provides beamformed samples for the various locations along receive scan lines or for receive beams.

The focus profile or profiles based on the speed of sound are used in transmit and/or receive beamforming. The beamformer controller calculates the relative delays and/or phases during beamformation using the speed of sound or loads pre-created profiles using the speed of sound. The focus or foci used during scanning are established by the beamformer focus profile.

In act 38, the ultrasound medical scanner or processor (e.g., image processor of the medical scanner) generates an image of the tissue from results of the scanning. The beamformed samples from scanning in any format (e.g., linear, sector, or Vector®) are used to generate an image. The beamformed samples are detected, such as a B-mode detector determining the intensity represented by the different beamformer samples. In other modes, scans of the same locations from different times are used to estimate the velocity, power, and/or variance of flow or motion from the beamformed samples. Any detection or mode of imaging may be used.

The detected data may be filtered temporally and/or spatially. The detected data may be scan converted, such as to a Cartesian grid format of a display. The detected data may be mapped to color values for display, such as grayscale values for B-mode imaging or values of different shades of different colors for color flow or Doppler imaging. An image representing spatial distribution of tissue response to acoustic energy is generated.

In one embodiment, the image is of the liver. For example, a B-mode image showing intensity of acoustic return as a function of a one, two, or three-dimensional distribution of locations is generated. As another example, a color flow or Doppler image showing flow of blood or fluid in the liver tissue is generated. In yet other embodiments, the image includes some locations from B-mode response and other locations from Doppler or flow response.

The image is responsive to or results from the data beamformed based on the speed of sound. The scanning for imaging is configured by the beamformer based on the speed of sound derived from the fat fraction. B-mode and/or Doppler scanning using the fat fraction-based speed of sound results in an image with fewer or less intense (noticeable) artifacts due to an incorrectly assumed speed of sound in the tissue.

The imaging is performed after configuring the beamformer based on the determined speed of sound. The imaging may continue without interruption from before to after the re-configuration due to a newly determined speed of sound. Alternatively, the user is notified of the change and a gap in imaging occurs. The imaging after the change in the beamformer configuration may provide diagnostic ultrasound images with greater diagnostic information as compared to the imaging before the change.

The ultrasound scanner or a display device displays the image. Other information may be included with the image representing the anatomy of the patient. For example, an annotation, highlighting, colorization, or overlay representing the value of the fat fraction is displayed.

In alternative embodiments, the generated image is stored or transferred over a computer network. For example, the image is transferred for storage in a computerized medical record for the patient of a medical records database.

FIG. 2 shows one embodiment of a system 10 for ultrasound medical imaging. The system 10 implements the method of FIG. 1 or other methods. Tissue, such as liver tissue, is scanned to measure the fat fraction of the patient. The fat fraction is used to configure the transmit beamformer 12 and/or receive beamformer 16 to operate using speed of sound appropriate for the fat fraction of the tissue.

The system 10 includes the transmit beamformer 12, a transducer 14, the receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, picture archiving and communications system (PACS) station, or other arrangement at a same location or distributed over a network for real-time or post acquisition imaging.

The transmit and receive beamformers 12, 16 form a beamformer for scanning (e.g., transmit and receive operations) using the transducer 14. Sequences of pulses are transmitted, and responses are received based on operation or configuration of the beamformer. The beamformer scans for measuring fat fraction and imaging tissue.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region may be scanned multiple times using different scan line angles, F numbers, and/or waveform center frequencies. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The transducer 14 is an array for generating acoustic energy from electrical waveforms. For an array, relative delays or phasing focus the acoustic energy. A given transmit event corresponds to transmission of acoustic energy by different elements at a substantially same time given the delays.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware, firmware, or software to apply relative delays, phases, and/or apodization to form one or more receive beams in response to each imaging transmission. The receive beamformer 16 outputs data representing spatial locations using the receive signals. Relative delays and/or phasing and summation of signals from different elements provide beamformation.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or another band.

In coordination with the transmit beamformer 12, the receive beamformer 16 generates data representing the region. By scanning the region of interest with ultrasound, data (e.g., beamformed samples) is generated. By repeating the scanning, ultrasound data representing the region at different times is acquired.

The receive beamformer 16 outputs beam summed data representing spatial locations. Data for a single location, locations along a line, locations for an area, or locations for a volume are output. Dynamic focusing may be provided. Data for different types of measures are acquired with a series of shared or interleaved scans. B-mode or Doppler scanning may be performed separately or using some of the same data. Scanning for fat fraction estimation may use image data or data acquired for B-mode or Doppler imaging or may use data from a scan just for fat fraction estimation.

The transmit and/or receive beamformers 12, 16 scan tissue in a patient based on a speed of sound. The beamformers 12, 16 are configured by one or more focus profiles 13 defining relative delays and/or phases between channels, waveforms, and/or element signals. The focus profiles 13 are based, in part, on the speed of sound. By selecting the focus profiles 13 based on the fat fraction, the speed of sound appropriate for the tissue of the patient is selected and used. Alternatively, the beamformers 12, 16 calculate the delays and/or phases in real time using value of the speed of sound. In either embodiment, the delay and/or phase profiles 13 have at least one different delay and/or phase due to the difference in the speed of sound.

Until the fat fraction is measured in a given instance, a default or previous speed of sound is used. After the fat fraction is measured, the speed of sound is changed. The changed speed of sound is used until a new measure of fat fraction occurs or until the tissue imaging is complete. Different speeds of sound are used in different or sequential scans.

The image processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof, or other now known or later developed device for detecting and processing information for display from beamformed ultrasound samples.

In one embodiment, the image processor 18 includes one or more detectors and a separate image processor. The separate image processor is a control processor, general processor, digital signal processor, application specific integrated circuit, field programmable gate array, network, server, group of processors, combinations thereof, or other now known or later developed device for calculating values of different types of parameters from beamformed and/or detected ultrasound data, for estimating a fat fraction from the values from the different types of measures, and for determining a speed of sound from the fat fraction. The separate image processor is configured by hardware, firmware, and/or software to perform any combination of one or more of the acts shown in FIG. 1.

The image processor 18 is configured to estimate a value for the fat fraction from a combination of different types of parameters. For example, a measured scatter parameter and a measured shear wave parameter are used. The different types of parameters are measured based on the transmit and receive sequences and calculation from the results. The values of the one or more measures of each of at least two of the types (e.g., scatter, attenuation, shear wave propagation, or axial ARFI) of parameters are determined. The beamformed samples output by the beamformer using one speed of sound are used for quantitative measurements (e.g., attenuation and backscatter), which are used to estimate the fat fraction.

The image processor 18 estimates the fat fraction based on the different types of parameters or measures of tissue reaction to different types of wave fronts. The estimation applies a machine-learnt classifier. The input values of the measures with or without other information are used by a learnt regressor model to output a value of the fat fraction. In other embodiments, the image processor 18 uses a weighted combination of the values of the parameters. A linear or non-linear mapping relates values of one or more parameters to the value of the fat fraction.

The image processor 18 is configured to set the speed of sound from the fat fraction. A value for the speed of sound or a beamformer focus profile is set based on the fat fraction. For example, a look-up table relates fat fraction values to speeds of sound values or focus profiles. The image processor 18 then controls the beamformers 12, 16 to use the speed of sound (e.g., value for speed of sound or focus profiles based on the speed of sound) for subsequent scanning and/or imaging. The image processor 18 may provide the speed of sound information to a beamformer controller, directly control the beamformers 12, 16, or provide the fat fraction to the beamformer controller, which uses the fat fraction to configure the beamformers 12, 16 to use the speed of sound indicated by the fat fraction.

The processor 18 is configured to generate one or more images. For example, a shear wave velocity, B-mode, contrast agent, M-mode, flow or color mode, ARFI, and/or another type of image is generated. The shear wave velocity, flow, or ARFI image may be presented alone or as an overlay or region of interest within a B-mode image. The shear wave velocity, flow, or ARFI data modulates the color at locations in the region of interest. Where the shear wave velocity, flow, or ARFI data is below a threshold, B-mode information may be displayed without modulation by the shear wave velocity. The image is of the tissue from beamformed samples output by the receive beamformer 16 using the fat fraction-based speed of sound.

Other information is included in the image or displayed sequentially or substantially simultaneously. For example, a tissue property estimate image is displayed at a same time as the other image. A value or values of the fat fraction map to display information. Where the fat fraction is measured at different locations, the values of the fat fraction may be generated as a color overlay in the region of interest in B-mode images. The shear wave velocity and fat fraction data may be combined as a single overlay on one B-mode image. Alternatively, the value of the fat fraction is displayed as text or a numerical value adjacent or overlaid on a B-mode or shear wave imaging image. The image processor 18 may be configured to generate other displays. For example, a shear wave velocity image is displayed next to a graph, text, or graphical indicators of the fat fraction. The fat fraction information is presented for one or more locations of the region of interest without being in a separate two or three-dimensional representation, such as where the user selects a location and the ultrasound scanner then presents the fat fraction for that location.

The image processor 18 operates pursuant to instructions stored in the memory 22 or another memory for fat fraction estimation, speed of sound determination, control of scanning based on the determined speed of sound, and/or imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a device, such as a CRT, LCD, projector, plasma, or other display for displaying one or two-dimensional images or three-dimensional representations. The two-dimensional images represent spatial distribution in an area. The three-dimensional representations are rendered from data representing spatial distribution in a volume. The display 20 is configured by the image processor 18 or other device by input of the data to be displayed as an image. The display 20 displays an image representing the tissue, such as the liver. The image is based on scanning with a speed of sound set based on the fat fraction of the tissue being imaged.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for ultrasound imaging with an ultrasound scanner, the method comprising:

estimating, by a processor, fat fraction for a liver of a patient, the fat fraction estimated from a combination of ultrasound measurements extracted from received ultrasound signals, the fat fraction estimated as a quantitative value;

determining, by the processor, a speed of sound in tissue of the liver from the quantitative value of the fat fraction;

configuring a beamformer of the ultrasound scanner based on the determined speed of sound; and imaging the liver of the patient with the beamformer as configured based on the determined speed of sound.

2. The method of claim 1 wherein estimating comprises estimating from scatter and attenuation as the measurements obtained from scanning the liver by the ultrasound scanner.

3. The method of claim 2 wherein the scanning the liver comprises scanning with the beamformer configured with a default speed of sound.

4. The method of claim 2 wherein other imaging for the estimating occurs during the estimating with another speed of sound and the imaging with the beamformer as configured based on the determined speed of sound occurs after the other imaging.

5. The method of claim 1 wherein determining the speed of sound comprises determining as a calculation by the processor with a function of the fat fraction.

6. The method of claim 1 wherein determining the speed of sound comprises determining the speed of sound with a look-up table relating the quantitative value of the fat fraction to the speed of sound.

7. The method of claim 1 wherein configuring comprises changing a default speed of sound to the determined speed of sound.

8. The method of claim 1 wherein imaging comprises beamforming samples from signals from elements of an array, where the beamforming uses a delay or phase profile based on the determined speed of sound.

9. The method of claim 1 wherein imaging comprises B-mode scanning of the liver and generating a B-mode image of the liver from results of the scanning, the beamformer used for the B-mode scanning.

10. A system for ultrasound medical imaging, the system comprising:

a transducer;

a beamformer configured to scan tissue in a patient, with the transducer, based on a first speed of sound in the tissue and a second speed of sound in the tissue;

an image processor configured to estimate a percentage of fat fraction of the tissue of the patient from beamformed samples output by the beamformer using the first speed of sound, to set the second speed of sound from the percentage of the fat fraction, and to generate an image of the tissue from beamformed samples output by the beamformer using the second speed of sound as set from the fat fraction; and a display configured to display the image of the tissue.

11. The system of claim 10 wherein the beamformer is configured to scan using a delay profile or a phase profile for elements of an array of the transducer, the delay profile or phase profile set at different times from the first and second speeds of sound.

12. The system of claim 10 wherein the image processor is configured to estimate the percentage of the fat fraction from attenuation and backscatter measured from the beamformed samples using the first speed of sound.

13. The system of claim 10 wherein the image processor is configured to set the second speed of sound from a look-up table relating percentages of the fat fractions to speeds of sound.

14. The system of claim 10 wherein the image processor is configured to generate the image as a B-mode image.

15. The system of claim 10 wherein the tissue comprises liver tissue and the fat fraction comprises fat fraction of the liver of the patient.

16. A method for optimized speed of sound setting in an ultrasound medical scanner, the method comprising:

measuring a fat fraction of tissue in a patient, the measuring of the fat fraction resulting in a calculated quantity for the fat fraction;

setting a beamformer focus profile based on the calculated quantity of the fat fraction;

scanning the tissue of the patient by the ultrasound medical scanner using the beamformer focus profile; and generating an image of the tissue from results of the scanning.

17. The method of claim 16 wherein measuring comprises measuring the fat fraction by the ultrasound medical scanner.

18. The method of claim 16 wherein setting comprises setting a delay or phase profile of a beamformer of the ultrasound medical scanner.

19. The method of claim 16 wherein setting comprises determining a speed of sound in the tissue from the calculated quantity of the fat fraction and setting the beamformer focus profile based on the determined speed of sound.

20. The method of claim 16 wherein scanning comprises beamforming with focus established by the beamformer focus profile.

* * * * *